(12) United States Patent
Pubill Coy et al.

(10) Patent No.: US 7,635,782 B1
(45) Date of Patent: Dec. 22, 2009

(54) STEREOSPECIFIC METHOD FOR THE PREPARATION OF DIOXA-BICYCLOOCTANE COMPOUNDS

(75) Inventors: Francisco Pubill Coy, Barcelona (ES); Anna Modolell Saladrigas, Barcelona (ES); Jose Repolles Moliner, Barcelona (ES)

(73) Assignee: Lacer, S.A., Barcelona (ES)

( * ) Notice: Subject to any disclaimer, the term of this patent is extended or adjusted under 35 U.S.C. 154(b) by 0 days.

(21) Appl. No.: 12/372,119

(22) Filed: Feb. 17, 2009

(30) Foreign Application Priority Data

Jul. 22, 2008 (EP) ................................. 08380221
Nov. 14, 2008 (EP) ................................. 08380318

(51) Int. Cl.
*C07D 493/04* (2006.01)
(52) U.S. Cl. ...................................... 549/464; 549/414
(58) Field of Classification Search ................. 549/464, 549/414
See application file for complete search history.

(56) References Cited

U.S. PATENT DOCUMENTS

2003/0225134 A1* 12/2003 Moliner et al. .............. 514/338

* cited by examiner

*Primary Examiner*—Bernard Dentz
*Assistant Examiner*—David E Gallis
(74) *Attorney, Agent, or Firm*—Oblon, Spivak, McClelland, Maier & Neustadt, L.L.P.

(57) ABSTRACT

This invention relates to a new method for the stereospecific thiocarboxylation of organic compounds for the preparation of compounds according to formula (I):

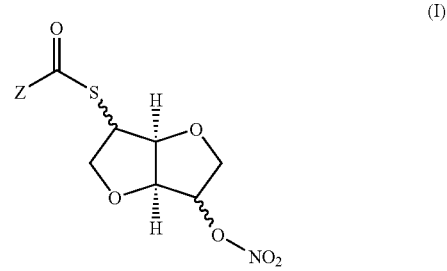

(I)

wherein a compound of formula (II):

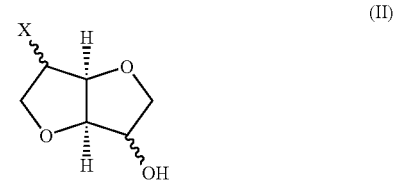

(II)

is reacted with a compound of formula (IIIa) or (IIIb):

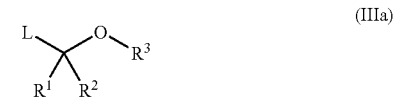

(IIIa)

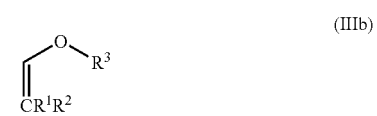

(IIIb)

then treating the obtained product with a thiocarboxylic acid or a salt thereof, and subsequently carrying out a nitration reaction.

13 Claims, No Drawings

STEREOSPECIFIC METHOD FOR THE PREPARATION OF DIOXA-BICYCLOOCTANE COMPOUNDS

FIELD OF THE INVENTION

The present invention relates to a new stereospecific method for the preparation of dioxa-bicyclooctane compounds.

BACKGROUND ART

The nitric acid esters of organic compounds, commonly known as nitrated organic compounds, are known and have been used as vasodilating agents for some time. Among these, the usefulness of mono- and di-nitrated isosorbide is well known, and furthermore, compounds with vascular and coronary activities based on substitution reactions of the free hydroxyl group of isosorbide mononitrate have been described.

Patent application WO 00/20420 describes isosorbide mononitrates wherein the free hydroxyl group is esterified with either carboxylic acids or with thioacids wherein said ester groups are in trans position with respect to the nitrate group.

Patent application WO 2005/037842 describes isosorbide mononitrates wherein the free hydroxyl group has been replaced by a wide range of substituents.

A particular class of compounds disclosed in these publications is represented by the following formula (A)

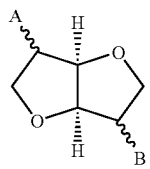

(A)

wherein one of A and B represents —$ONO_2$ and the other represents —S—CO—R, wherein R is a $C_{1-4}$ alkyl group, an aryl group or an aralkyl group, eventually substituted. According to these publications the disclosed dioxa-bicyclooctane compounds may be prepared by thioacetylation of a compound of formula (B):

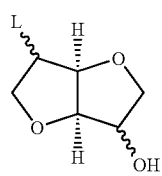

(B)

wherein L represents a leaving group, isolating the thioacetylated product by chromatography, carrying out a nitration reaction, and then purifying the compounds of interest by another chromatographic treatment.

This preparation method affords less than 20% overall yield and involves chromatographic treatments after the thioacetylation step as well as after the nitration reaction. This chromatographic treatment is extremely disadvantageous for industrial-scale synthetic preparations. Furthermore, both the low yield and the purification by chromatography are highly undesirable from an economic point of view.

SUMMARY OF THE INVENTION

In view of the above drawbacks, it is an object of the present invention to provide a new preparation method for dioxa-bicyclooctane compounds, which does not involve a chromatographic treatment and results in higher overall yields.

The present inventors have developed a novel stereospecific preparation method for dioxa-bicyclooctane compounds in which surprisingly no chromatographic purification is required and products of high purity and in good yields are obtained.

The present inventors have further applied this new synthetic route to prepare a group of compounds represented by formula (IA) or (IB):

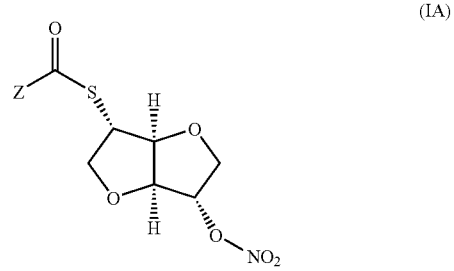

(IA)

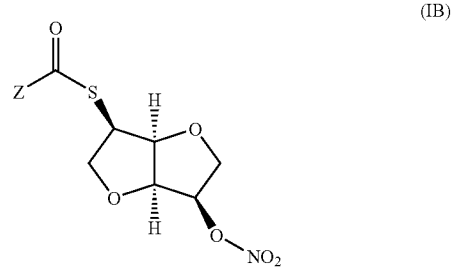

(IB)

These novel compounds have been found to surprisingly show excellent usability for the treatment of cardiovascular and coronary dysfunctions.

DETAILED DESCRIPTION OF THE INVENTION

The present invention provides a method for the preparation of compounds according to formula (I):

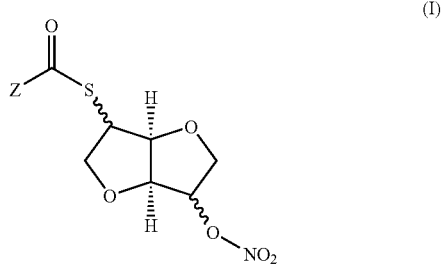

(I)

wherein z represents a $C_{1-6}$-alkyl, $C_{2-6}$-alkenyl, $C_{3-8}$-cycloalkyl, aryl, heteroaryl, aryl $C_{1-6}$-alkyl, or heteroaryl-$C_{1-6}$- alkyl group, optionally substituted by one to three groups independently chosen from the group consisting of halogen, $C_{1-6}$-alkyl and $C_{1-6}$-alkylthio, comprising reacting a compound of formula (II):

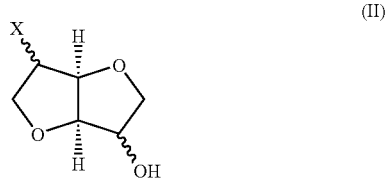

wherein X represents halogen, cyano, methanesulfonyloxy, p-toluenesulfonyloxy or trifluoromethanesulfonyloxy, with a compound of formula (IIIa) or (IIIb):

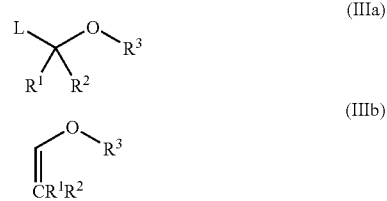

wherein L represents halogen, cyano, methanesulfonyloxy, p-toluenesulfonyloxy or trifluoromethanesulfonyloxy;

and $R^1$, $R^2$ and $R^3$ independently from each other represent hydrogen, $C_{1-6}$-alkyl, $C_{2-6}$-alkenyl, $C_{3-8}$-cycloalkyl, $C_{4-8}$-cycloalkenyl, ($C_{1-6}$-alkyl)-$C_{3-8}$-cycloalkyl, ($C_{1-6}$-alkyl)-$C_{4-8}$-cycloalkenyl, phenyl or ($C_{1-6}$-alkyl)-phenyl, or $R^2$ and $R^3$ together form a 5-, 6- or 7-membered saturated or unsaturated ring, then treating the obtained product, preferably without isolation, with a thiocarboxylic acid of formula (IV) or a salt thereof:

wherein Z is as defined above, and subsequently carrying out a nitration reaction.

The above-mentioned compounds of formula (II) are either commercially available or can be obtained for example by an addition or substitution reaction with the respective dianhydro sugar compound, such as isomannide, isosorbide or isoidide, as it is for example described in the publications of Chemical Abstract Services, the Beilstein Encyclopedia of organic products, or in WO 00/20420.

In the preparation method according to the present invention the compounds of formula (IIIa) or (IIIb) react with the free hydroxyl group of the compound of formula (II).

In the subsequent thiocarboxylation reaction the group X is replaced by the thiocarboxylic acid of formula (IV) or a salt thereof. This reaction appears to take place as a bimolecular nucleophilic substitution ($S_N2$) reaction since inversion of the configuration in the carbon atom is observed.

As mentioned above, the process of the invention is stereospecific in the sense that when in the starting product of formula (II) the X group is trans to the hydroxyl group, the resulting product of formula (I) has a thiocarboxylate Z—C(=O)S group which is cis to the nitrate group. When a starting product with cis configuration is used, in the resulting product the thiocarboxylate Z—C(=O)S group is trans to the nitrate group.

In an embodiment of the preparation method of the present invention, in formula (I) the thiocarboxylate Z—C(=O)S group is trans to the nitrate group.

In another embodiment of the preparation method of the present invention, in formula (I) the thiocarboxylate Z—C(=O)S group is cis to the nitrate group.

In another embodiment of the preparation method of the present invention, in formula (II) L represents a halogen atom or a p-toluenesulfonyloxy group, preferably a p-toluenesulfonyloxy group.

The thiocarboxylation reaction can be carried out with the thiocarboxylic acid of formula (IV) or a salt thereof. The use of the salt is preferred, and examples thereof are salts with an alkali metal or an earth alkali metal. Specially preferred alkali metals or earth alkali metals are sodium, potassium, cesium, magnesium and calcium, whereof potassium is preferred.

The subsequent nitration reaction simplifies the previously known method disclosed for example in WO 00/20420 because the obtained products do not need to be purified by chromatography. This is highly advantageous not only under economic considerations but also in view of the easier handling of the synthesis. The nitration reaction can be carried out by addition of any nitrating mixture such as nitric acid in the presence of any dehydrating agent such as sulfuric acid or acetic anhydride.

Surprisingly, the method of the present invention provides higher yield and purity compared to the state of the art documents. The overall yield for the preparation of compounds of formula (I) from compounds of formula (II) is increased compared to the method disclosed in WO 00/20420 and can even exceed 40%. Also the purity of the compounds obtained by the method of the present invention makes unnecessary to undertake a step of purification by chromatography as it is disclosed in this document.

Furthermore, as has been outlined above, the stereochemistry at the C2 position of compound (II) is inverted during the preparation. Accordingly, if the starting compound is an isomannide or an isoidide derivative, the end product will be the corresponding isosorbide derivative. However, if the starting compound (II) relates to an isosorbide derivative, the end product will be either the respective isomannide or isoidide derivative.

The general terms used above have the meaning indicated:

The term "$C_{1-6}$-alkyl" refers to a straight or branched hydrocarbon chain radical having 1 to 6 carbon atoms and which is attached to the rest of the molecule by a single bond, e.g., methyl, ethyl, n-propyl, isopropyl, n-butyl, iso-butyl, sec-butyl, t-butyl, n-pentyl, n-hexyl, etc.

The term "$C_{2-6}$-alkenyl" refers to a straight or branched hydrocarbon chain radical, having 2 to 6 carbon atoms and at least one double bond of either E or Z stereochemistry where applicable, e.g., vinyl, allyl, 1-butenyl, 2-butenyl, and 2-methyl-2-propenyl.

The term "$C_{3-8}$-cycloalkyl" refers to an alicyclic group having 3 to 8 carbon atoms, e.g., cyclopropyl, cyclobutyl, cyclopentyl and cyclohexyl.

The term "$C_{4-8}$-cycloalkenyl" refers to an alicyclic group having 4 to 8 carbon atoms, e.g., cyclopentenyl, cyclohexenyl, cycloheptenyl and cyclooctenyl.

The term "halogen" refers to fluorine, chlorine, bromine or iodine, whereof bromine is preferred.

"Aryl" refers to an aromatic hydrocarbon radical, preferably with 6 to 14 carbon atoms, e.g., phenyl, naphthyl, fluorenyl, or phenanthryl, whereby said radicals are unsubstituted or substituted by one or more substituents independently of one another, preferably up to three, primarily one or two substituents, especially those chosen from unsubstituted, mono- or di-substituted amino, halogen, unsubstituted or substituted alkyl, free, etherified or esterified hydroxy, nitro, cyano, free or esterified carboxy, alkanoyl, unsubstituted, N-mono- or N,N-di-substituted carbamoyl, amidino, guanidino, mercapto, phenylthio, phenylsulfinyl, phenylsulfonyl, ethenyl, phenyl, methylthio, acetyl, methylmercapto ($CH_3S-$), trifluoromethylmercapto ($CF_3S-$), trifluoromethylsulfonyl, and methylenedioxy bound to adjacent carbon atoms of the ring; aryl is for example phenyl which is unsubstituted or is substituted by one or two substituents, independently of one another, chosen from the group consisting of amino, acetylamino, fluorine, chlorine, bromine, methyl, ethyl, propyl, or t-butyl, trifluoromethyl, hydroxy, methoxy, ethoxy, benzyloxy, and cyano, or (as an alternative or in addition to the above group of substituents) n-decyloxy, carbamoyl, N-methyl- or N-tert-butylcarbamoyl, acetyl, phenyloxy, trifluoromethoxy or 1,1,2,2-tetrafluoroethoxy, ethoxycarbonyl, methyl mercapto, trifluoromethylmercapto, hydroxymethyl, 1-hydroxyethyl, methylsulfonyl, trifluoromethylsulfonyl, phenylsulfonyl, 2-methyl-pyrimidin-4-yl, oxazol-5-yl, 2-methyl-1,3-dioxolan-2-yl, pyrazol-3-yl, methyl-pyrazol-3-yl and methylenedioxy bound to two adjacent carbon atoms; especially preferred are one or two substituents chosen independently of one another from methyl, chlorine or bromine, and trifluoromethyl. Aryl in the form of phenyl which is substituted by methylene dioxy is preferably 3,4-methylene dioxyphenyl. Aryl is most preferably phenyl which is preferably unsubstituted or substituted by one or more substituents chosen independently of one another from the group consisting of methyl, ethyl, n-propyl, i-propyl, t-butyl, fluorine, chlorine, bromine, methoxy, trifluoromethyl; phenyl is most preferably unsubstituted or substituted by one or two substituents chosen independently of one another from the group consisting of methyl, ethyl, isopropyl or t-butyl, bromine, chlorine, fluorine, and trifluoromethyl.

"Heteroaryl" refers to an unsaturated heterocyclic radical and is mono-, bi- or tricyclic, preferably monocyclic, whereby, one or more, preferably one to four, especially one or two, most preferably one carbon atom(s) of a corresponding aryl radical are replaced by a hetero atom chosen from the group consisting of nitrogen, oxygen and sulfur, whereby the binding ring has preferably 4 to 12, especially 5 to 7 ring atoms; whereby heteroaryl said radical is unsubstituted or is substituted by one or more, especially 1 to 3, substituents chosen independently from the group consisting of the above-mentioned substituents of aryl; and it is in particular a heteroaryl radical chosen from the group consisting of imidazolyl, thienyl, furyl, pyranyl, thianthrenyl, isobenzofuranyl, benzofuranyl, chromenyl, 2H-pyrrolyl, pyrrolyl, imidazolyl, benzimidazolyl, pyrazolyl, thiazolyl, isothiazolyl, oxazolyl, isoxazolyl, pyridyl, pyrazinyl, pyrimidinyl, pyridazinyl, indolizinyl, isoindolyl, 3H-indolyl, indazolyl, triazolyl, tetrazolyl, purinyl, quinolizinyl, isoquinolyl, quinolyl, phthalazinyl, naphthyridinyl, quinoxalyl, quinazolinyl, cinnolinyl, pteridinyl, carbazolyl, phenanthridinyl, acridinyl, perimidinyl, phenanthrolinyl, furazanyl, etc.

The term "aryl-$C_{1-6}$-alkyl" refers to an aryl group attached to a $C_{1-6}$-alkyl group, e.g., phenylmethyl, phenylethyl, phenylpropyl, phenylbutyl, phenylpentyl, phenylhexyl, naphthylmethyl, naphthylethyl, naphthylbutyl, fluorenylmethyl, fluorenylethyl, fluorenylbutyl, phenanthrylethyl and phenanthrylbutyl, which are unsubstituted or substituted as explained above for aryl. Preferably aryl-$C_{1-6}$-alkyl relates to phenylmethyl, phenylpropyl, phenylpentyl, and naphthylmethyl, whereof phenylpropyl is most preferred.

The term "heteroaryl-$C_{1-6}$-alky" refers to a heteroaryl group which is attached to a $C_{1-6}$-alkyl group, e.g., imidazolylmethyl, imidazolylethyl, imidazolylbutyl, thienylmethyl, thienylethyl, thienylbutyl, furylmethyl, furylethyl, furylbutyl, furylhexyl, pyranylethyl, pyranylbutyl, pyrrolylethyl, pyrrolylethyl, pyrrolylbutyl, pyrrolylhexyl, imidazolylethyl, imidazolylbutyl, pyridylethyl, pyridylbutyl, pyrazinylethyl, and pyrazinylbutyl, which are unsubstituted or substituted as explained above for heteroaryl. Preferably heteroaryl-$C_{1-6}$-alkyl relates to thienylmethyl, furylmethyl, pyranylmethyl, imidazolylmethyl, pyridylmethyl, and pyridylpropyl, whereof pyridylmethyl is most preferred.

The term "5-, 6- or 7-membered ring" refers to an alicyclic ring containing either no or at least one double bond, e.g., cyclopentane, cyclohexane, cyclopentene, cyclohexene, etc.

In an embodiment of the present invention, residue Z both in compound (I) and (IV) represents a $C_{1-6}$-alkyl, $C_{2-6}$-alkenyl, aryl, or heteroaryl group, which group may be unsubstituted or substituted. Preferably Z represents a $C_{1-6}$-alkyl group, more preferably methyl, ethyl, n-propyl, or n-butyl, and most preferably methyl.

In a further embodiment of the present invention in formula (IIIa) L represents halogen, and $R^1$, $R^2$ and $R^3$ independently represent hydrogen or $C_{1-6}$ alkyl.

In another embodiment of the present invention in formula (IIIb) $R^1$ represents hydrogen or $C_{1-6}$ alkyl and $R^2$ and $R^3$ together with the atoms to which they are attached and with the carbon atom attached to the oxygen form a 5-, 6- or 7-membered ring.

In a preferred embodiment of the present invention formula (IIIa) represents bromomethyl-methylether and formula (IIIb) represents 3,4-dihydro-2H-pyran or methyl-vinylether.

For example, when 2-(p-toluenesulfonyloxy)isomannide (2) as a starting compound of formula (II):

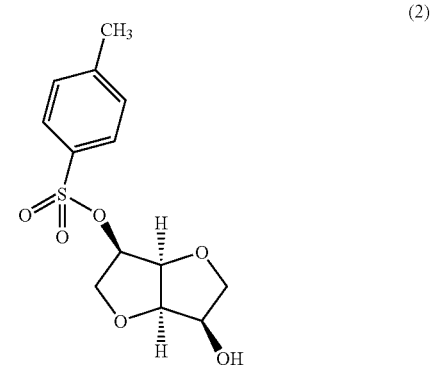

(2)

is reacted with 3,4-dihydro-2H-pyran the following compound (3) is obtained, which represents another embodiment of the invention:

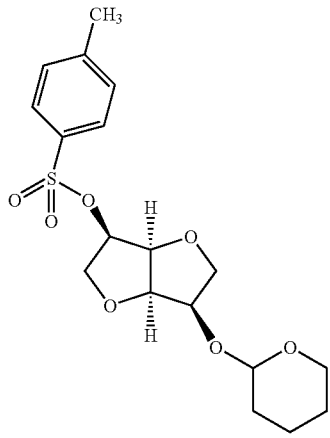

(3)

For the subsequent thiocarboxylation with thioacetate as an example of compound (IV), compound (3) as described above does not need to be isolated and can be transformed into compound (4) in a one-pot-reaction. This compound (4) represents another aspect of the invention:

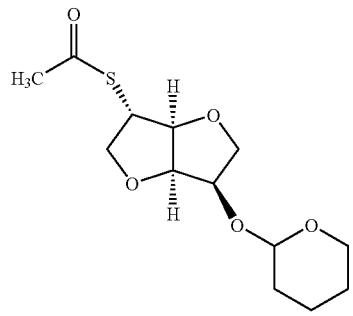

(4)

Similarly, when 2-(p-toluenesulfonyloxy)isomannide (5) as a starting compound of formula (II):

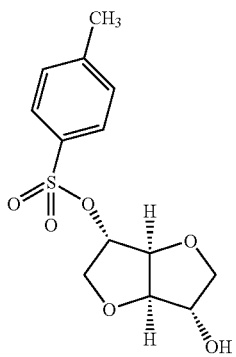

(5)

is reacted with 3,4-dihydro-2H-pyran the following compound (6) is obtained, which represents another embodiment of the invention:

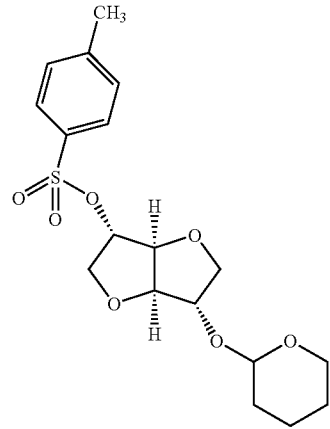

(6)

For the subsequent thiocarboxylation with thioacetate as an example of compound (IV), compound (6) as described above does not need to be isolated and can be transformed into compound (7) in a one-pot-reaction. This compound (7) represents another aspect of the invention:

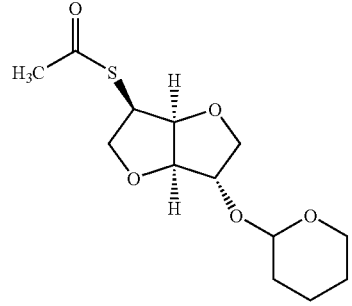

(7)

By the present method novel dioxa-bicycloctane compounds can be prepared. These new compounds form a further aspect of the present invention and are represented by the following formula (I):

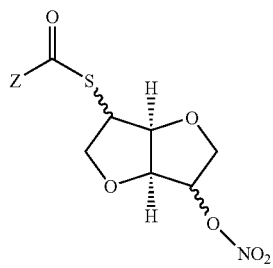

(I)

wherein both the nitrate and the thiocarboxylate are trans or both are cis with regard to the bridgehead hydrogens, i.e.

compounds according to formula (IA) ("isoidide derivative") and formula (IB) ("isomannide derivative"):

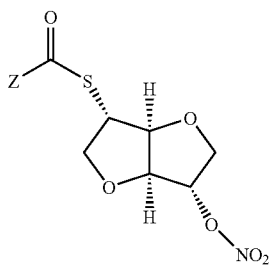

(IA)

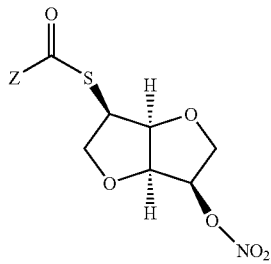

(IB)

Especially preferred representatives of compounds (IA) and (IB) are those wherein Z represents a $C_1$-$C_3$ alkyl group or a $C_3$ alkenyl group more preferably a methyl:

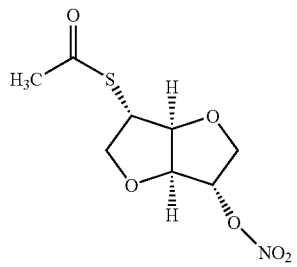

(18)

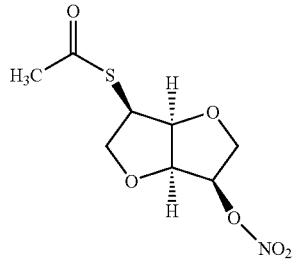

(15)

The working examples included in the present specification describe in detail suitable processes to obtain several of the compounds according to general formula (I). In the light of these examples, it is within the general knowledge of the expert in the field to obtain the compounds not explicitly exemplified by suitable modifications of the working examples. It is also obvious for the expert in the field that these examples are only illustrative and should not be taken as a limitation of the scope of the invention.

EXAMPLES

The compounds obtained in the examples described below are identified by their proton ($^1$H-NMR) and carbon-13 ($^{13}$C-NMR) nuclear magnetic resonance spectroscopic data.

The Nuclear Magnetic Resonance spectra were recorded using a Varian Gemini-2000 apparatus.

The operating frequency and the solvent used to record the spectra are indicated in the $^1$H-NMR spectra. The signal's positions are indicated in δ (ppm) and the signal from the solvent's protons is taken as a reference. The reference values were 7.24 ppm for deuterated chloroform and 2.49 ppm for hexadeuterated dimethyl sulfoxide. The signal obtained for tetramethylsilane's (TMS) protons is occasionally taken as an internal standard, with a reference value of 0 ppm. Within brackets are indicated the number of protons corresponding to each signal measured by electronic integration and the type of signal using the following abbreviations: s (singlet), d (doublet), t (triplet), q (quadruplet), dd (doublet of doublets), ddd (doublet of doublet of doublets), bs (broad signal), m (multiplet), cs (complex signal), s.a. $D_2O$ (simplifies upon deuteration), d.a. $D_2O$ (disappears upon deuteration).

The $^{13}$C-NMR spectra indicate the working frequency and the solvent used to run the spectrum. The position of the signals is indicated in δ (ppm), using the central signal of the solvent as reference. The reference values are 77.00 ppm for deuterated chloroform and 39.50 ppm for hexadeuterated dimethyl sulfoxide.

When HPLC analyses were performed to determine the purity or stability of some of the samples, the following conditions were used: Symmetry C18 Column, 5 mcm, 150× 3.9 mm; Temperature: 30° C.; Eluents: A: 100% water, B: 100% acetonitrile; Composition gradient: 0 to 100% acetonitrile in 30 min and 5 further min with 100% acetonitrile.

In the experimental part, the following abbreviations are used:

| | |
|---|---|
| AcOEt | ethyl acetate |
| ar | aromatic |
| DMSO-$d_6$ | hexadeuterated dimethylsulfoxide |
| DMF | N,N-dimethylformamide |
| Hx | hexane |
| HPLC | high performance liquid chromatography |
| MeOH | methyl alcohol |
| THP | tetrahydropyranyl |
| Ts | tosyl (para-toluenesulfonyl) |

Example 1

Synthesis of 2-acetylthio-isosorbide 5-mononitrate (5)

Step 1: Preperation of isomannide monotosylate (2)

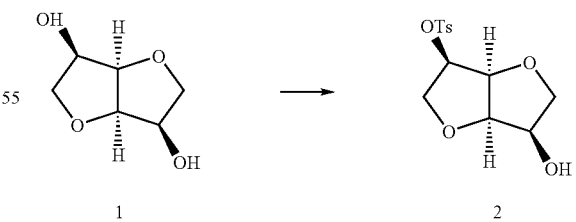

In a 250 L reactor, 15.0 Kg (102.6 mol) of isomannide (1) are mixed with 61.8 L of water. The mixture is stirred until total dissolution and cooled to 5-10° C. A solution of 27.05 Kg (115.5 mol) of tosyl chloride in 72 L of toluene is added and the reaction mixture is vigorously stirred and cooled at 3-5° C. A solution of potassium hydroxide 7.45 Kg (132.8 mol) in 25.0 L of water is slowly added, maintaining the vigorous stirring and the temperature between 3 and 5° C. The mixture is stirred for 4 h at 4-5° C. Without heating the suspension, the resulting solid is filtered and washed with a volume between 6 and 9 L of toluene. The filtered solid is mixed with 102 L of toluene and heated to 90° C. until total dissolution. Between 10 and 20 L of toluene are distilled. The toluenic solution is cooled at 3-5° C. for 2 h, filtered and washed with a volume between 6 and 9 L of toluene. The solid obtained is dried in a vacuum oven at 40° C. yielding 22.8 Kg (74%) of isomannide monotosylate (2), which is identified by its spectroscopic data.

$^{1}$H-NMR (DMSO-d$_{6}$, 200 MHz): 7.83-7.64 (cs, 2H, CH$_{ar}$), 7.36-7.27 (cs, 2H, CH$_{ar}$), 4.92-4.78 (cs, 1H, CHOTs), 4.50-4.40 (cs, 2H, CHCHOTs, CHCHOH), 4.40-4.20 (cs, 1H, CHOH), 4.02-3.86 (cs, 2H, H—CHCHOTs, H—CHCHOH), 3.80-3.68 (cs, 1H, H—CHCHOTs), 3.56-3.44 (cs, 1H, H—CHCHOH), 2.41 (s, 3H, CH$_{3}$), 2.39 (cs, 1H, OH, d.a. D$_{2}$O).

$^{13}$C-NMR (DMSO-d$_{6}$, 50 MHz): 145.3 (C$_{ar}$) 132.9 (C$_{ar}$) 129.9 (2CH$_{ar}$), 127.9 (2CH$_{ar}$), 81.3 (CHCHOH), 80.0 (CHCHOTs), 78.3 (CHOTS), 73.8 (CH$_{2}$CHOH), 72.2 (CHOH), 69.9 (CH$_{2}$CHOTs), 21.5 (CH$_{3}$).

Step 2: Preparation of 5-(tetrahydropyran-2-yl)-2-(4-toluenesulfonyl)isomannide (3)

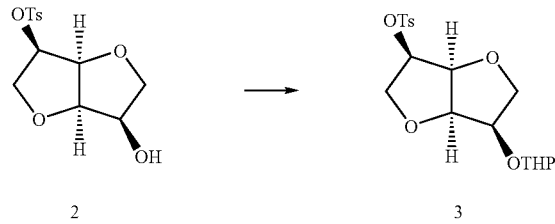

In a 250 L reactor are loaded 21.5 Kg of isomannide monotosylate (2), 129 L of toluene and 6.74 Kg (7.31 L, 80.12 mol) of 3,4-dihydro-2H-pyran. The mixture is cooled at 17-18° C. and a solution of 26 g (430 mL, 0.27 mol) of methanesulfonic acid in 400 mL of dichloromethane is added. Stirring is maintained until the reaction has finished (ca. 1 h, reaction control is performed by thin layer chromatography Hx/AcOEt 1:1). The mixture is washed with 25 L of sodium bicarbonate saturated aqueous solution. The aqueous phase is separated and the organic phase is washed with 17 L of sodium bicarbonate saturated aqueous solution and 17 L of water. The aqueous phase is decanted and the toluene is distilled under reduced pressure, maintaining the internal temperature at 50° C. Addition of 21.5 L of N,N-dimethylformamide is followed by distillation to eliminate the remaining toluene. The solution of the title compound in N,N-dimethylformamide (27.5 Kg of (3) estimated by HPLC) obtained is used in the next step without purification.

After subjecting 15.3 g of the crude reaction product (isolated after drying at reduced pressure) to silica gel flash chromatography (Hx/AcOEt 2:1), 13.38 g of the title compound are obtained.

$^{1}$H-NMR (CDCl$_{3}$, 200 MHz): 7.83-7.76 (cs, 2H, CH$_{ar}$), 7.36-7.27 (cs, 2H, CH$_{ar}$), 4.92-4.78 (cs, 1H, CHOTS), 4.74-4.58 (cs, 1H, CH$_{THP}$), 4.50-4.38 (cs, 2H, CHCHOTS, CHCHOTHP), 4.32-4.12 (cs, 1H, CHOTHP), 4.04-3.40 (cs, 6H, CH$_{2}$CHOTs, CH$_{2}$CHOH, OCH$_{2}$ $_{THP}$), 2.41 (s, 3H, CH$_{3}$), 1.90-1.40 (cs, 6H, 3CH$_{2}$ $_{THP}$).

$^{13}$C-NMR (CDCl$_{3}$, 50 MHz): 145.0 (C$_{ar}$), 133.2 (C$_{ar}$), 129.8 (2CH$_{ar}$), 127.9 (2CH$_{ar}$), 99.9 and 98.3 (CH$_{THP}$), 81.4 and 80.3 (CHCHOTHP), 80.2 and 79.8 (CHCHOTs), 78.9 and 78.4 (CHOTS), 77.9 and 76.0 (CHOTHP), 71.5 and 70.2 (CH$_{2}$CHOTs), 70.0 and 69.7 (CH$_{2}$CHOTHP), 62.7 and 62.4 (CH$_{2}$O$_{THP}$), 30.3 and 30.2 (CH$_{2}$ $_{THP}$), 25.2 and 25.1 (CH$_{2}$ $_{THP}$), 21.6 (COCH$_{3}$), 19.4 and 19.2 (CH$_{2}$ $_{THP}$).

Step 3: Preparation of 5-(tetrahydropyran-2-yl)-2-acetylthio-isosorbide (4)

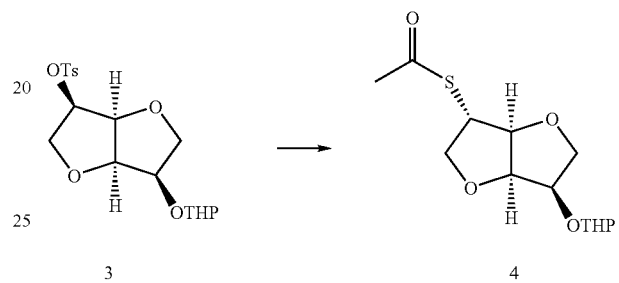

16.34 Kg (143.1 mol) of potassium thioacetate are added to the solution of 5-(tetrahydropyran-2-yl)-2-(4-toluenesulfonyl)isomannide (3) (27.5 Kg, 71.6 mol) in N,N-dimethylformamide prepared in the previous step. Heating at 95-100° C. is maintained until the reaction has finished (ca. 2 h, reaction control is performed by thin layer chromatography Heptane/AcOEt 1:2). Cooling at 45° C. is followed by addition of 52 L of toluene and 23 L of sodium bicarbonate saturated aqueous solution. Water (20 L) is added and the two phases stirred for 10 min at 20-30° C.

The aqueous phase is separated (62 L) and the organic phase is washed with 43 L of water. The aqueous phase is decanted (62 L) and washing is performed with 2×23 L of sodium bicarbonate saturated aqueous solution. Toluene is distilled from the organic phase in order to azeotropically remove the remaining water. The solution of the title compound in toluene (19.05 Kg of (4) estimated by HPLC) is stored cold and used in the next step without purification.

After subjecting 24.69 g of the crude reaction product (isolated after drying at reduced pressure) to silica gel flash chromatography (Hx/AcOEt 3:1), 15.91 g of the title compound are obtained.

$^{1}$H-NMR (CDCl$_{3}$, 200 MHz): 4.78-4.58 (cs, 1H, CH$_{TPH}$) 4.58-4.40 (cs, 2H, CHCHOTHP, HCHS), 4.36-4.14 (cs, 2H, H—CHCHS, CHOTHP), 4.06-3.42 (cs, 6H, H—CHCHS, H—CHCHS, H—CHS, CH$_{2}$CHOTHP, CH$_{2}$O$_{THP}$), 2.31 (s, 3H, COCH$_{3}$), 1.86-1.40 (cs, 6H, 3CH$_{2}$ $_{THP}$).

$^{13}$C-NMR (CDCl$_{3}$, 50 MHz): 194.3 (CO), 99.6 and 98.3 (CH$_{THP}$), 87.4 and 87.3 (CHCHS), 81.8 and 80.6 (CHCHOTHP), 77.9 and 76.0 (CHOTHP), 73.9 and 73.8 (CH$_{2}$CHS), 71.2 and 69.2 (CH$_{2}$CHOTHP), 62.5 (CH$_{2}$O$_{THP}$), 49.0 and 48.8 (CHS), 30.5 (COCH$_{3}$) 30.3 (CH$_{2}$ $_{THP}$), 25.2 and 25.1 (CH$_{2}$ $_{THP}$) 119.3 and 19.2 (CH$_{2}$ $_{THP}$).

Step 4: Preparation of 2-acetylthio-isosorbide 5-mononitrate (5).

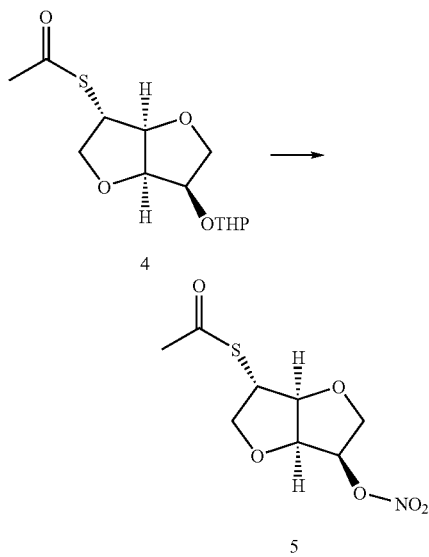

In a 250 L reactor, 43 Kg (421.2 mol) of acetic anhydride are cooled at 5° C. and 13.4 Kg (9.44 L, 127 mol) of 60% nitric acid are slowly added, maintaining the temperature at 5° C. The nitrating mixture thus obtained is stored cold. 20 L of toluene are added over 48.85 Kg of the toluenic solution obtained in the previous step (19.05 Kg (66.06 mol) of 5-(tetrahydropyran-2-yl)-2-acetylthio-isosorbide (4)). The nitrating mixture is slowly added onto the toluenic solution, maintaining the temperature between 27 and 35° C. After the addition, the mixture is maintained at 25-30° C. until the reaction has finished (ca. 2-3 h, reaction control is performed by thin layer chromatography Hx/AcOEt 4:6). The toluenic phase is washed with 20.6 L of sodium chloride saturated aqueous solution. The aqueous phase is decanted (55 L), MeOH is added (5.0 L) and the solution is stirred for 20 min. The mixture is washed with 4×20.6 L of sodium bicarbonate saturated aqueous solution and the organic phase is distilled at reduced pressure maintaining the internal temperature at 50° C. In order to completely eliminate the toluene, 10 L of isopropyl alcohol are added and distilled at reduced pressure. This operation is repeated with 10 L more of isopropyl alcohol. The obtained product is recrystallized from 15.4 L of isopropyl alcohol containing 30% of water. After drying at reduced pressure at 40° C., 8.2 Kg of the title compound are obtained.

$^1$H-NMR (200 MHz, CDCl$_3$): 5.34 (1H, ddd, J=5.4 Hz, J=2.8 Hz, J=5.4 Hz, H—CONO$_2$), 4.89 (1H, dd, J=5.4 Hz, J=4.8 Hz, H—C—OCH$_2$), 4.45 (1H, d, J=4.8 Hz, H—C—OCH$_2$), 4.20 (1H, dd, J=4.6 Hz, J=9.8 Hz, H—CHCHS), 4.14-4.02 (2H, cs, H—CHCHONO$_2$, H—CS), 3.96-3.86 (1H, cs, H—CHCHS), 3.90 (1H, dd, J=11.4 Hz, J=5.4 Hz, H—CHCHONO$_2$), 2.36 (3H, s, CH$_3$).

$^{13}$C-NMR (50 MHz, CDCl$_3$): 194.2 (C=O), 88.5 (CHOC), 81.5 (CHOC), 1.3 (CHONO$_2$), 73.5 (CH$_2$CHS), 69.3 (CH$_2$CONO$_2$), 48.0 (CHS), 30.6 (CH$_3$).

Example 2

Synthesis of 2-acetylthio-isosorbide 5-mononitrate (5)

Step 1: Preparation of 5-methoxymethyl-2-(4-toluenesulfonyl) isomannide (6).

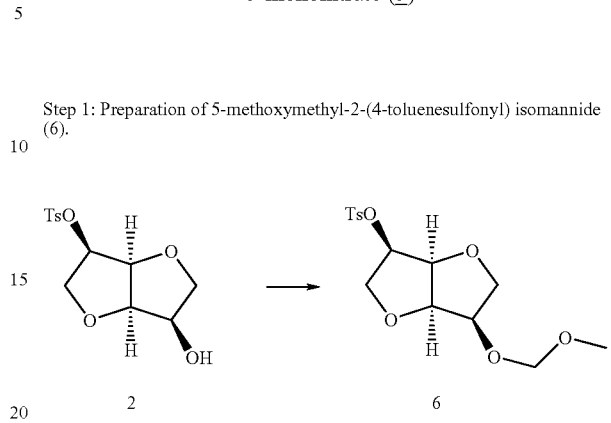

To a solution of 10 g (33.3 mmol) of 2-(4-toluenesulfonyl) isomannide (2) in 80 mL of DMF, 14 mL (10.12 g, 100.0 mmol) of triethylamine are added. Then, 6.10 mL (8.32 g, 66.6 mmol) of bromomethyl methyl ether are slowly added, resulting in a slight temperature increase. The mixture is stirred in a bath at 100° C. for 43 hours. The solvent is eliminated under reduced pressure, 300 mL of water are added, and the mixture is extracted with 3×250 mL of CHCl$_3$. The organic phases are combined, dried over anhydrous MgSO$_4$, filtered and concentrated under reduced pressure. After subjecting the crude reaction product to silica gel column chromatography (Hx:AcOEt 3:2), 2.60 g (7.55 mmol) of the title product are obtained.

$^1$H-NMR (CDCl$_3$, 200 MHz): 7.88 (dd, 2H, J=6.6 Hz, 1.8 Hz, CH$_{ar}$), 7.31 (dd, 2H, J=8.0 Hz, 0.8 Hz, CH$_{ar}$), 4.95-4.80 (m, 1H, CHOTS), 4.66 (dd, 2H, J=11.8 Hz, 7.0 Hz, OCH$_2$O), 4.55-4.40 (m, 2H, 2CH—O—C), 4.18-3.85 (cs, 3H, H—CHCHOTs, H—CHCHOCH$_2$OCH$_3$, CHOCH$_2$OCH$_3$), 3.78 (dd, 1H, J=9.6 Hz, 7.6 Hz, H—CHCHOTS), 3.60 (dd, 1H, J=8.4 Hz, 8.4 Hz, H—CHCHOCH$_2$OCH$_3$), 3.35 (s, 3H, OCH$_3$), 2.42 (s, 3H, CH$_3$).

$^{13}$C-NMR (CDCl$_3$, 50 MHz): 145.1 (C$_{ar}$), 133.2 (C$_{ar}$), 129.8 (2 CH$_{ar}$), 128.0 (2CH$_{ar}$), 96.7 (OCH$_2$O), 80.8 (O—CHCHOCH$_2$OCH$_3$), 80.0 (O—CHCHOTs), 78.6 (CHOTS), 77.7 (CHOCH$_2$OCH$_3$), 70.8 (CH$_2$—CHOCH$_2$OCH$_3$), 70.2 (CH$_2$—CHOTS), 55.8 (OCH$_3$), 21.6 (CH$_3$).

Step 2: Preparation of 5-methoxymethyl-2-acetylthio-isosorbide (7)

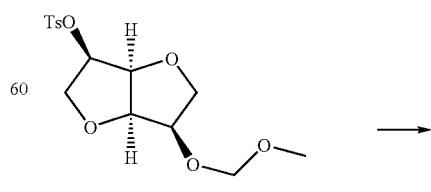

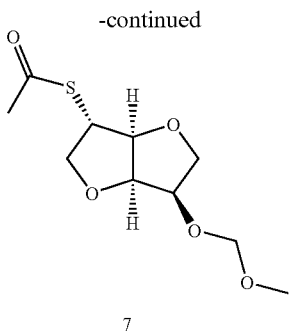

7

To a solution of 3.9 g (11.33 mmol) of 5-methoxymethyl-2-(4-toluenesulfonyl)isomannide (6) in 32 mL of DMF, 5.2 g (45.3 mmol) of potassium thioacetate are added and the mixture stirred at 100° C. (bath temperature) and under nitrogen atmosphere for 3 h. The mixture is cooled, diluted with 120 mL of toluene and washed with 3×130 mL of NaHCO$_3$ saturated aqueous solution. The organic phase is dried over anhydrous MgSO$_4$, filtered and concentrated under reduced pressure. After subjecting the crude product to silica gel column chromatography (Hx:AcOEt 3:2), 1.3 g (5.26 mmol, yield: 46%) of the title compound as an oil are obtained.

$^1$H-NMR (CDCl$_3$, 200 MHz): 4.69 (dd, 2H, J=15.0 Hz, 6.6 Hz, OCH$_2$O), 4.54 (dd, 1H, J=4.4 Hz, 4.4 Hz, CHOCH$_2$OCH$_3$), 4.48 (dd, 1H, J=6.6 Hz, 1.0 Hz, CHCHS), 4.30-4.20 (m, 1H, H—CHCHS), 4.22-4.10 (cs, 1H, CHOCH$_2$OCH$_3$), 4.05-3.92 (cs, 2H, CHS, H—CHCHOCH$_2$OCH$_3$), 3.84 (dd, 1H, J=7.0 Hz, J=3.0, H—CHCHOCH$_2$OCH$_3$), 3.66 (dd, 1H, J=8.4 Hz, 8.4 Hz, H—CHCHS), 3.37 (s, 3H, OCH$_3$), 2.32 (s, 3H, COCH$_3$).

$^{13}$C-NMR (CDCl$_3$, 50 MHz): 194.2 (CO), 96.6 (OCH$_2$O), 87.3 (O—CHCHS), 81.1 (O—CHCHOCH$_2$OCH$_3$), 77.7 (CHOCH$_2$OCH$_3$), 73.9 (CH$_2$—CHS), 70.4 (CH$_2$—CHCHOCH$_2$OCH$_3$), 55.8 (OCH$_3$), 49.0 (CHS), 30.6 (COCH$_3$).

Step 3: Preparation of 2-acetylthio-isosorbide 5-mononitrate (5)

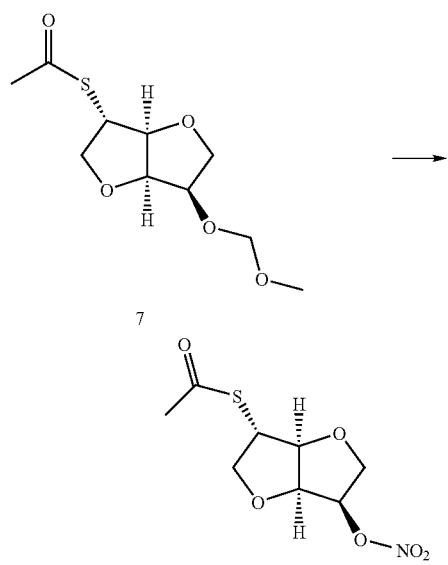

To a mixture of 4.3 mL of acetic anhydride and 1 mL of acetic acid cooled to 5° C., 1 mL of nitric acid (60%) is carefully added. Then, 3.5 mL of the resulting mixture are slowly added to a solution of 0.85 g (3.44 mmol) of 5-methoxymethyl-2-acetylthio-isosorbide (7) in 4 mL of acetic acid. The mixture is kept below 5° C., avoiding freezing, for 5 h and then left to stand at room temperature, diluted with 60 mL of toluene and washed with 50 mL of saturated NaCl solution. The organic phase is washed with 55 mL of a saturated solution of NaHCO$_3$ containing 15 mL of MeOH and then with 4×50 mL of a saturated solution of NaHCO$_3$. The organic phase is dried over anhydrous MgSO$_4$, filtered and concentrated under reduced pressure. 0.52 g of the crude product are obtained in which the title compound is identified as the major product.

Example 3

Synthesis of 2-acetylthio-isosorbide 5-mononitrate (5)

Step 1: Preparation of 5-(1-ethoxyethyl)-2-(4-toluenesulfonyl)isomannide (8)

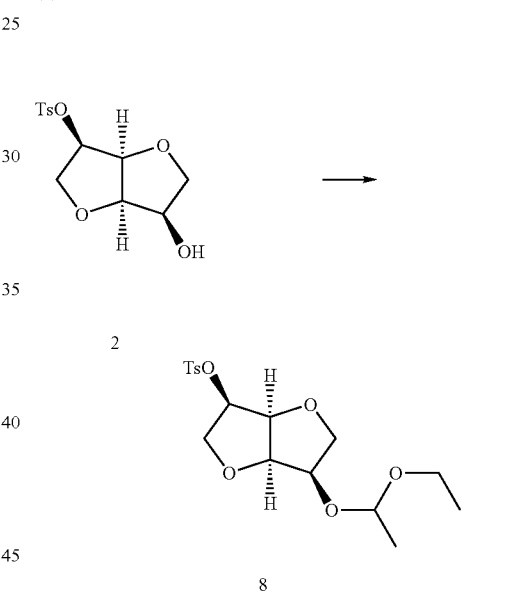

To a solution of 19.2 g (0.266 mol, 25.5 mL) of ethyl vinyl ether in 250 mL of CH$_2$Cl$_2$, cooled in an ice bath under nitrogen atmosphere, 20.0 g (66.6 mmol) of 2-(4-toluenesulfonyl)isomannide (2) and 4.0 g (16.0 mmol) of pyridinium p-toluenesulfonate are added. Cold stirring protected from light is performed for 30 minutes and then for 2 h at room temperature. The mixture is diluted with 250 mL of ethyl ether and washed with 300 mL of a NaCl solution. The organic phase is dried over anhydrous MgSO$_4$, filtered and concentrated under reduced pressure. The process yields 24.6 g (67.7 mmol) of an oil identified as the two diastereomers of the title compound.

$^1$H-NMR (CDCl$_3$, 200 MHz): 7.79 (dd, 2H, J=6.6 Hz, 1.8 Hz, CH$_{ar}$), 7.31 (dd, 2H, J=8.0 Hz, 0.8 Hz, CH$_{ar}$), 4.90-4.70 (m, 2H, CHOTs, OCHO), 4.50-4.40 (m, 1H, CHCHOTS), 4.45-4.30 (m, 1H, CHCHOCH(CH$_3$)O), 4.30-4.15 (m, 1H, CHOCH(CH$_3$)O), 4.00-3.85 (cs, 2H, H—CHCHOTs H—CHCHOCH(CH$_3$)O), 3.77 (dd, 1H, H—CHCHOTs), 3.62-3.38 (cs, 3H, OCH$_2$, H—CHCHOCH(CH$_3$)O), 2.41 (s,

3H, CH$_3$—C$_{ar}$), 1.29 (dd, 3H, J=6.2 Hz, 5.0 Hz, C$\underline{H}_3$CH), 1.15 (q, 3H, J=7.0 Hz, C$\underline{H}_3$CH$_2$O).

$^{13}$C-NMR (CDCl$_3$, 50 MHz): 145.1 (C$_{ar}$), 133.2 (C$_{ar}$), 129.8 (2CH$_{ar}$), 127.9 (2CH$_{ar}$), 99.4 and 99.3 (OCHO), 81.2 and 80.8 ($\underline{C}$HCHOCH(CH$_3$)O), 80.0 and 79.8 ($\underline{C}$HCHOTs), 78.9 and 78.6 (CHOTs), 74.3 and 73.9 ($\underline{C}$HOCH(CH$_3$)O), 71.2 and 70.5 ($\underline{C}$H$_2$—CHOCH(CH$_3$)O), 70.3 and 70.1 ($\underline{C}$H$_2$—CHOTs C$_1$), 61.1 and 60.4 ($\underline{C}$H$_2$CH$_3$), 21.6 (CH$_3$—C$_{ar}$), 19.8 and 19.7 ($\underline{C}$H$_3$—CHO), 15.2 and 15.1 ($\underline{C}$H$_3$—CHO).

Step 2: Preparation of 5-(1-ethoxyethyl)-2-acetylthio-isosorbide (9)

To a solution of 25.2 g (67.67 mmol) of 5-(1-ethoxyethyl)-2-(4-toluenesulfonyl)isomannide (8) in 250 mL of DMF, 30.9 g (0.271 mol) of potassium thioacetate are added and the mixture stirred at 100° C. (bath temperature) under nitrogen atmosphere for 4 h. The mixture is cooled, diluted with 500 mL of toluene and washed with 3×600 mL of saturated NaHCO$_3$ solution. The organic phase is dried over anhydrous MgSO$_4$, filtered and concentrated under reduced pressure. After subjecting the crude reaction product to silica gel column chromatography (Hx:AcOEt 3:1), 8.3 g (30.1 mmol) of 2-acetylthio-isosorbide (24) and the title compound are obtained.

5-(1-ethoxyethyl)-2-acetylthio-isosorbide (9)

$^1$H-NMR (CDCl$_3$, 200 MHz): 4.90-4.75 (m, 1H, OCHO), 4.50-4.35 (m, 2H, C$\underline{H}$CHS, C$\underline{H}$CHOCH(CH$_3$)O), 4.30-4.10 (m, 2H, CHS, C$\underline{H}$OCH(CH$_3$)O), 4.00-3.70 (cs, 3H, 2 $\underline{H}$—CHCHS, $\underline{H}$—CHCHOCH(CH$_3$)O), 3.64-3.38 (cs, 3H, OCH$_2$, $\underline{H}$—CHCHOCH(CH$_3$)O), 2.28 (s, 3H, CH$_3$CO), 1.29 (dd, 3H, J=7.6 Hz, 5.4 Hz, C$\underline{H}_3$CH), 1.15 (m, 3H, C$\underline{H}_3$CH$_2$O).

$^{13}$C-NMR (CDCl$_3$, 50 MHz): 194.1 (C=O), 99.2 and 99.1 (OCHO), 87.2 and 87.1 ($\underline{C}$HCHS), 81.4 and 81.1 ($\underline{C}$HCHOCH(CH$_3$)O), 74.3, 73.9 and 73.7 ($\underline{C}$H$_2$—CHS, $\underline{C}$HOCH(CH$_3$)O), 70.8 and 69.9 ($\underline{C}$H$_2$—CHOCH(CH$_3$)O), 61.0 and 60.3 ($\underline{C}$H$_2$CH$_3$), 49.0 and 48.7 (CHS), 30.5 (CH$_3$COS), 19.8 and 19.7 ($\underline{C}$H$_3$CHO), 15.1 and 15.0 ($\underline{C}$H$_3$CH$_2$).

Step 3: Preparation of 1-acetylthio-isosorbide mononitrate (5)

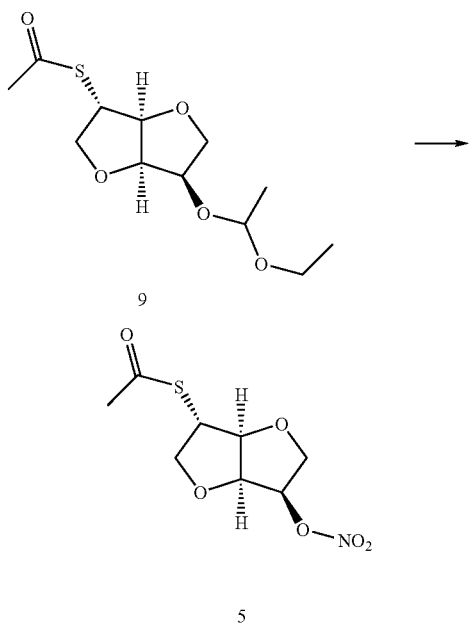

To a mixture of 4.3 mL of acetic anhydride and 1 mL of acetic acid cooled to 5° C., 1 mL of nitric acid is carefully added. Then, 4.0 mL of the previous mixture are slowly added to a solution of 1.0 g (3.63 mmol) of the crude reaction product obtained in the previous step in 5 mL of acetic acid. This mixture is stirred at a temperature under 5° C., avoiding freezing, for 4 hours and then left at room temperature, diluted with 60 mL of toluene and washed with 50 mL of saturated NaCl solution. The organic phase is washed with 55 mL of a saturated solution of NaHCO$_3$ containing 15 mL of MeOH and then with 4×50 mL of a saturated solution of NaHCO$_3$. The organic phase is dried over anhydrous MgSO$_4$, filtered and concentrated under reduced pressure. 0.95 g of the crude reaction product are obtained in which the title compound is identified as the major product.

Example 4

Synthesis of 2-acetylthio-isomannide 5-mononitrate (15)

Step 1: Preparation of 2-(4-toluenesulfonyl) isosorbide (11) and 5-(4-toluenesulfonyl) isosorbide (12)

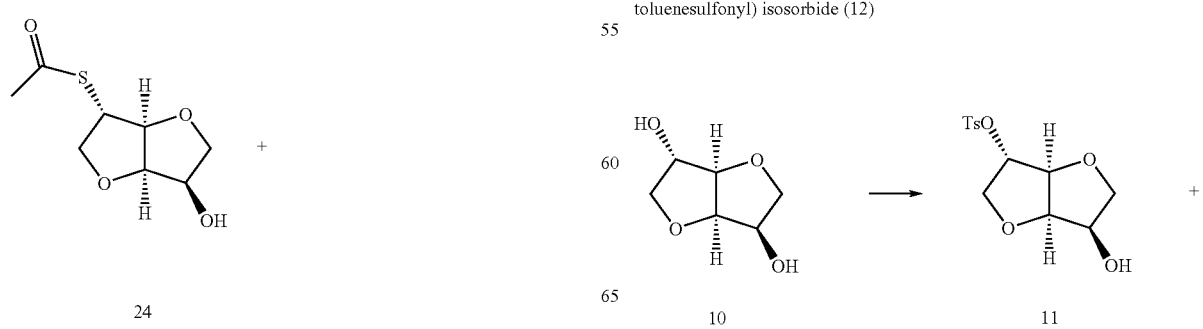

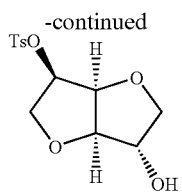

12

To a solution of 20.0 g (0.137 mol) of isosorbide (10) in 80 mL of water cooled in an ice-salt bath was dropwise added a solution of 28.7 g (0.150 mol) of 4-toluenesulfonyl chloride in 140 mL of toluene. A solution of potassium hydroxide (10 g KOH in 34 mL of water) is carefully added, keeping the temperature below 5° C. Cold stirring is performed for 6 h, and then at room temperature overnight. The aqueous phase is separated and the solvent is eliminated under reduced pressure. The resulting crude reaction product is dissolved in 300 mL of CHCl$_3$ dried over anhydrous MgSO$_4$, filtered and concentrated under reduced pressure. After subjecting the crude reaction product to silica gel column chromatography (AcO-Et:Hx 2:1), 11.4 g (38.0 mmol) of 2-(4-toluenesulfonyl)isosorbide (11) and 2.3 g (7.66 mmol) of 5-(4-toluenesulfonyl) isosorbide (12) are obtained.

2-(4-toluenesulfonyl)isosorbide (11)

$^1$H-NMR (DMSO-d$_6$, 200 MHz): 7.81 (d, 2H, J=8.4 Hz, CH$_{ar}$), 7.48 (d, 2H, J=8.0 Hz, CH$_{ar}$), 5.00-4.85 (cs, 1H, OH), 4.80-4.75 (cs, 1H, CHOTS), 4.50-4.35 (m, 2H, CHCHOTS, C HCHOH), 4.15-4.00 (m, 1H, CH—OH), 3.80 (d, 2H, J=2.2 Hz, CH$_2$CHOTs), 3.67 (dd, 1H, J=6.2 Hz, 8.4 Hz, H—CHCHOH), 3.26 (dd, 1H, J=8.4 Hz, 7.6 Hz, H—CH—CHOH), 2.41 (s, 3H, CH$_3$).

$^{13}$C-NMR (DMSO-d$_6$, 50 MHz): 144.3 (C$_{ar}$), 131.5 (C$_{ar}$), 129.3 (2CH$_{ar}$), 126.5 (2CH$_{ar}$), 83.7 (CHCHOTs), 83.5 (CHOTS), 80.5 (CHOH), 71.2 (CH$_2$—CHOTs), 70.5 (CHOH), 70.4 (CH$_2$—CHOH), 20.0 (CH$_3$).

5-(4-toluenesulfonyl)isosorbide (12)

$^1$H-NMR (DMSO-d$_6$, 200 MHz): 7.79 (d, 2H, J=8.4 Hz, CH$_{ar}$), 7.46 (d, 2H, J=8.4 Hz, CH$_{ar}$), 5.18 (d, 1H, J=4.4 Hz, OH), 4.92 (dd, 1H, J=11.2 Hz, 6.0 Hz, CHOTs), 4.45 (dd, 1H, J=4.8 Hz, 4.8 Hz, CHCHOTs), 4.19 (d, 1H, J=4.0 Hz, C HCHOH), 4.10-3.90 (cs, 1H, CH—OH), 3.75-3.60 (cs, 3H, 2CH$_2$CHOH, H—CHCHOTs), 3.55-3.40 (m, 1H, H—CHCHOTs), 2.41 (s, 3H, CH$_3$).

$^{13}$C-NMR (DMSO-d$_6$, 50 MHz): 144.0 (C$_{ar}$), 131.7 (C$_{ar}$), 129.1 (2CH$_{ar}$), 126.5 (2CH$_{ar}$), 86.7 (CHCHOH), 78.6 and 78.4 (CHOTs, CHCHOTs), 74.4 (CHOH), 73.7 (CH$_2$—CHOH), 67.6 (CH$_2$—CHOTs), 20.0 (CH$_3$).

Step 2: Preparation of 5-(tetrahydropyran-2-yl)-2-(4-toluenesulfonyl) isosorbide (13)

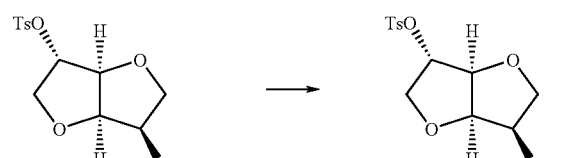

11 → 13

To a solution of 4.3 g (51.5 mmol, 4.63 mL) of 3,4-dihydro-2H-pyran in 80 mL of CH$_2$Cl$_2$ cooled in an ice bath under nitrogen atmosphere, are added 5.0 g (16.6 mmol) of 2-(4-toluenesulfonyl)isosorbide (11) and 0.9 g (3.6 mmol) of pyridinium p-toluenesulfonate. Cold stirring protected from light is then performed for 30 min and then at room temperature for 5 h. The mixture is diluted with 170 mL of ethyl ether and washed with 150 mL of a NaCl solution. The organic phase is dried over anhydrous MgSO$_4$, filtered and concentrated under reduced pressure. Toluene is added and the solvent is eliminated under reduced pressure to remove the remaining traces of CH$_2$Cl$_2$. This process yields 6.3 g (16.4 mmol) of the two diastereomers of the title compound as an oil.

$^1$H-NMR (DMSO-d$_6$, 200 MHz): 7.82 (d, 2H, J=8.0 Hz, CH$_{ar}$), 7.48 (d, 2H, J=8.2 Hz, CH$_{ar}$), 4.80 (s, 1H, C HCHOTHP), 4.66-4.43 (cs, 2H, CHOTs, CH$_{THP}$), 4.45-4.35 (m, 1H, CHCHOTs), 4.15-4.05 (m, 1H, CHOTHP), 3.85-3.75 (cs, 4H, CH$_2$CHOTs, CH$_2$O$_{THP}$), 3.50-3.30 (cs, 2H, C H$_2$CHOTHP), 2.41 (s, 3H, CH$_3$), 1.80-1.27 (cs, 6H, 3CH$_{2\,THP}$).

$^{13}$C-NMR (DMSO-d$_6$, 50 MHz): 144.3 (C$_{ar}$), 131.5 (C$_{ar}$), 129.3 (2CH$_{ar}$), 126.5 (2CH$_{ar}$), 96.8 and 96.5 (CH$_{THP}$), 83.8 and 83.7, 83.2 and 83.0 (CHOTs, CH—CHOTs,), 80.1 and 79.2 (CHCHOTHP), 75.9 and 74.3 (CHOTHP), 71.2, 69.5 and 67.6 (CH$_2$CHOTs, CH$_2$CHOTHP), 60.5 and 59.9 (CH$_2$O$_{THP}$), 28.9 (CH$_{2\,THP}$), 23.8 (CH$_{2\,THP}$), 20.0 (CH$_3$—C$_{ar}$), 17.9 and 17.5 (CH$_{2\,THP}$).

Step 3: Preparation of 5-(tetrahydropyran-2-yl)-2-acetylthio-isomannide (14)

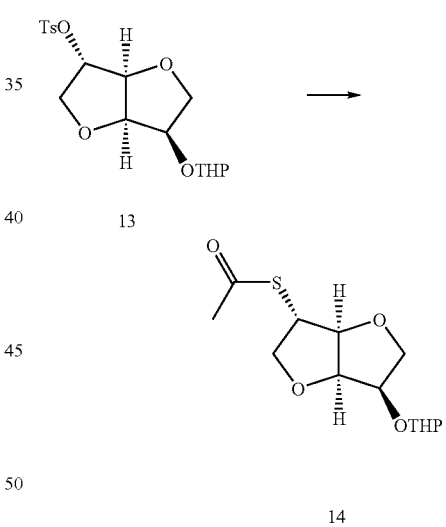

13 → 14

To a solution of 5.0 g (12.97 mmol) of 5-(tetrahydropyran-2-yl)-2-(4-toluenesulfonyl)isosorbide (13) in 33 mL of DMF, 5.9 g (51.9 mmol) of potassium thioacetate are added. The mixture is stirred at 100° C. (bath temperature) under nitrogen atmosphere for 23 h and then cooled, diluted with 100 mL of toluene and washed with 3×150 mL of a saturated solution of NaHCO$_3$. The organic phase is dried over anhydrous MgSO$_4$, filtered and concentrated under reduced pressure. After subjecting the crude reaction product to silica gel column chromatography (Hx:AcOEt 1:1), 2.3 g (7.98 mmol) of an oil identified as the two diastereomers of the title compound are obtained.

$^1$H-NMR (DMSO-d$_6$, 200 MHz): 4.67 (s, 1H, C HCHOTHP), 4.65-4.50 (m, 1H, CHCHS), 4.60-4.45 (m, 1H,

CHO$_{THP}$), 4.30-4.10 (cs, 1H, C$\underline{H}$OTHP), 3.90-3.70 (cs, 3H, C$\underline{H}_2$O$_{THP}$, CHS), 3.60-3.50 (m, 1H, H—CH—CHS), 3.50-3.35 (cs, 2H, C$\underline{H}_2$—CHOTHP), 2.32 (s, 3H, CH$_3$—C$_{ar}$), 1.80-1.27 (cs, 6H, 3C$\underline{H}_{2\ THP}$).

$^{13}$C-NMR (DMSO-d$_6$, 50 MHz): 194.0 (CO), 97.0 and 96.4 (CH$_{THP}$), 81.1 and 80.9+80.8 and 80.0 ($\underline{C}$H—CHS, $\underline{C}$H—CHO), 76.6 and 74.9 ($\underline{C}$HOTHP), 71.2 and 70.9+70.3 and 68.6 ($\underline{C}$H$_2$—CHS, $\underline{C}$H$_2$—CHOTHP), 60.5 and 59.9 ($\underline{C}$H$_2$O$_{THP}$), 45.4 and 44.7 ($\underline{C}$HS), 29.3 (CH$_{2\ THP}$) 28.9 (CH$_{2\ THP}$), 23.8 ($\underline{C}$H$_3$CO), 17.9 and 17.6 (CH$_{2\ THP}$).

Step 4: Preparation of 2-acetylthio-isomannide 5-mononitrate (15)

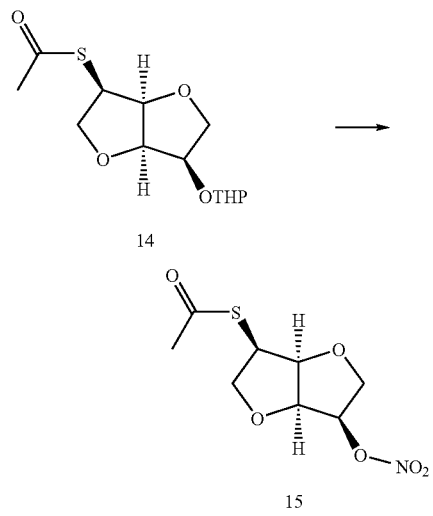

To a mixture of 4.3 mL of acetic anhydride and 1 mL of acetic acid cooled to 5° C., 1 mL of nitric acid (60%) is carefully added. The resulting mixture is slowly added to a solution of 2.3 g (7.98 mmol) of 5-(tetrahydropyran-2-yl)-2-acetylthio-isomannide (14) in 8 mL of acetic acid. The mixture is kept under 5° C., avoiding freezing, for 4 h then left at room temperature, diluted with 60 mL of toluene and washed with 50 mL of saturated NaCl solution. The organic phase is washed with 55 mL of a saturated solution of NaHCO$_3$ containing 15 mL of MeOH and then with 4×50 mL of saturated NaHCO$_3$. The organic phase is dried over anhydrous MgSO$_4$, filtered and concentrated under reduced pressure. After subjecting the crude reaction product to silica gel column chromatography (Hx:AcOEt 3:1), 0.63 g (2.53 mmol) of the title compound are obtained as an oil.

$^1$H-NMR (CDCl$_3$, 200 MHz): 5.33 (ddd, 1H, J=8.4 Hz, 5.4 Hz, 2.8 Hz, CHONO$_2$), 4.91 (dd, 1H, J=4.8 Hz, 4.8 Hz, C$\underline{H}$CHONO$_2$), 4.55 (dd, 1H, J=4.8 Hz, 4.8 Hz, C$\underline{H}$CHS), 4.20-3.80 (m, 4H, CHS, $\underline{H}$—CHCHS, C$\underline{H}_2$—CHONO$_2$), 3.56 (dd, 1H, J=8.0 Hz, 11.2 Hz, $\underline{H}$—CHCHS), 2.34 (s, 3H, C$\underline{H}_3$CO).

$^{13}$C-NMR (CDCl$_3$, 50 MHz): 194.5 (C=O), 83.4 ($\underline{C}$HCHS), 82.2 ($\underline{C}$H—CHONO$_2$), 81.6 (CHONO$_2$), 71.8 ($\underline{C}$H$_2$—CHS), 69.6 ($\underline{C}$H$_2$—CHONO$_2$), 44.7 (CHS), 30.4 ($\underline{C}$H$_3$CO).

Example 5

Synthesis of 5-acetylthio-isoidide 2-mononitrate (18)

Step 1: Preparation of 2-(tetrahydropyran-2-yl)-5-(4-toluenesulfonyl) isosorbide (16)

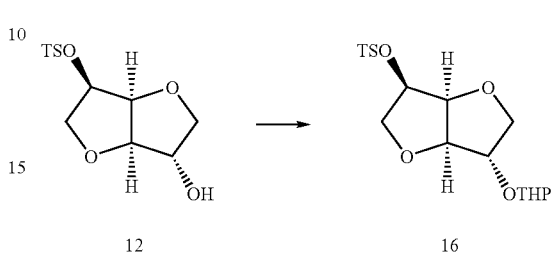

To a solution of 2.8 g (33.0 mmol, 3.0 mL) of 3,4-dihydro-2H-pyran in 60 mL of CH$_2$CO$_2$ cooled in an ice bath under nitrogen atmosphere, 3.3 g (11.0 mmol) of 5-(4-toluenesulfonyl)isosorbide (12) and 0.6 g (2.4 mmol) of pyridinium p-toluenesulfonate are added. Cold stirring protected from light is performed for 30 min and then at room temperature for 5 h. The mixture is diluted with 100 mL of ethyl ether, and washed with 120 mL of a semisaturated NaCl solution. The organic phase is dried over anhydrous MgSO$_4$, filtered and concentrated under reduced pressure. This process yields 4.1 g (10.7 mmol) of an oil identified as the two diastereomers of the title compound.

$^1$H-NMR (DMSO-d$_6$, 200 MHz): 7.79 (d, 2H, J=8.4 Hz, CH$_{ar}$), 7.47 (d, 2H, J=8.0 Hz, CH$_{ar}$), 5.00-4.85 (m, 1H, CHOTs), 4.70-4.60 (cs, 1H, CH$_{THP}$), 4.49 (dd, 1H, J=4.4 Hz, 4.4 Hz, C$\underline{H}$CHOTs), 4.12 (d, 1H, J=3.0 Hz, C$\underline{H}$CHOTHP), 3.90-3.60 (cs, 2H, CH$_{2\ THP}$), 3.60-3.30 (cs, 2H, C$\underline{H}_2$—CHOTs), 2.41 (s, 3H, CH$_3$), 1.80-1.30 (cs, 6H, 3CH$_{2\ THP}$).

$^{13}$C-NMR (DMSO-d$_6$, 50 MHz): 144.0 (C$_{ar}$), 131.7 (C$_{ar}$), 129.1 (2CH$_{ar}$), 126.5 (2CH$_{ar}$), 96.4 and 96.0 (CH$_{THP}$), 85.2 and 84.2 ($\underline{C}$HCHOTHP), 79.1 and 78.8, 78.7 and 78.5 ($\underline{C}$HOTs, $\underline{C}$HCHOTs), 78.3 and 78.2 ($\underline{C}$HOTHP), 72.7 and 71.7 ($\underline{C}$H$_2$—CHOTHP), 67.9 and 67.8 ($\underline{C}$H$_2$—CHOTs), 60.9 and 60.6 (CH$_2$O$_{THP}$), 29.2 and 29.1 (CH$_{2\ THP}$), 23.7 (CH$_{2\ THP}$), 20.0 (CH$_3$), 18.0 and 17.9 (CH$_{2\ THP}$).

Step 2: Preparation of 2-(tetrahydropyran-2-yl)-5-acetylthio-isoidide (17)

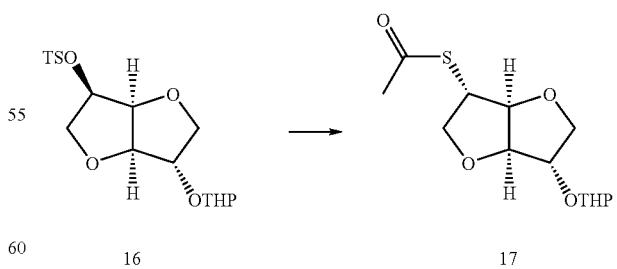

To a solution of 2.8 g (7.26 mmol) of 2-(tetrahydropyran-2-yl)-5-(4-toluenesulfonyl)isosorbide (16) in 20 mL of DMF, 3.32 g (29.06 mmol) of potassium thioacetate are added. The mixture is stirred at 115° C. (bath temperature) under nitrogen atmosphere for 22 h, cooled, diluted with 70 mL of toluene and washed with 3×80 mL of a saturated solution of NaHCO$_3$. The organic phase is dried over anhydrous MgSO$_4$, filtered, and concentrated under reduced pressure. After subjecting the crude reaction product to silica gel column chromatography (Hx:AcOEt 3:1), 1.2 g (4.16 mmol) of an oil identified as the two diastereomers of the title compound are obtained.

$^1$H-NMR (DMSO-d$_6$, 200 MHz): 4.75-4.60 (cs, 1H, C HOTHP), 4.55-4.40 (cs, 2H, CHCHS, CH$_{THP}$), 4.20-4.12 (cs, 1H, CHCHOTHP), 4.00 (ddd, 1H, J=9.6 Hz, J=5.2 Hz, J=1.6 Hz, CHS), 3.85-3.70 (cs, 3H, CH$_2$THP, H—CHCHS), 3.64 (dd, 1H, J=9.8 Hz, 2.6 Hz, H—CHCHS), 2.34 (s, 3H, CH$_3$), 1.75-1.30 (cs, 6H, THP).

$^{13}$C-NMR (DMSO-d$_6$, 50 MHz): 193.2 (CO), 96.5 and 96.1 (CH$_{THP}$), 85.5 and 85.4, 85.1 and 84.2 (CHCHOTHP, CHCHS), 79.0 and 78.4 (CHOTHP), 71.9 and 71.0, 70.3 (CH$_2$—CHS, CH$_2$—CHOTHP), 60.9 and 60.6 (CH$_2$O$_{THP}$), 46.7 and 46.6 (CHS), 29.5 (CH$_2$ $_{THP}$), 29.1 (CH$_2$ $_{THP}$), 23.8 (CH$_3$), 18.1 and 17.9 (CH$_2$ $_{THP}$).

Step 3: Preparation of 5-acetylthio-isoidide 2-mononitrate (18)

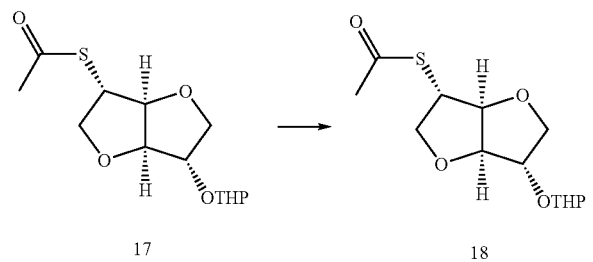

To a mixture of 4.3 mL of acetic anhydride and 1 mL of acetic acid cooled to 5° C., 1 mL of nitric acid (60%) is carefully added. Then, 4.5 mL of the resulting mixture is slowly added to a solution of 1.2 g (4.16 mmol) of 2-(tetrahydropyran-2-yl)-5-acetylthio-isoidide (17) in 6 mL of acetic acid. The mixture is kept under 5° C., avoiding freezing, for 4 h, then left to reach room temperature, diluted with 50 mL of toluene and washed with 40 mL of saturated NaCl solution. The organic phase is washed with 40 mL of a saturated solution of NaHCO$_3$ containing 15 mL of MeOH and with 4×40 mL of a saturated solution of NaHCO$_3$. The organic phase is dried over anhydrous MgSO$_4$, filtered and concentrated under reduced pressure. After subjecting the crude reaction product to silica gel column chromatography (CHCl$_3$:Hx 4:1), 0.64 g (2.57 mmol) of the title compound as an oil are obtained.

$^1$H-NMR (CDCl$_3$, 200 MHz): 5.32 (dd, 1H, J=4.4 Hz, 2.2 Hz, CHONO$_2$), 4.60 (s, 2H, CHCHS, CHCHONO$_2$), 4.20-4.05 (m, 2H, CH$_2$—CHONO$_2$), 4.05-3.95 (m, 2H, H—CHCHS, CHS), 3.78 (dd, 1H, J=9.6 Hz, 2.8 Hz, H—CHCHS), 2.32 (s, 3H, CH$_3$CO).

$^{13}$C-NMR (CDCl$_3$, 50 MHz): 193.9 (C=O), 87.3 and 84.1 (CHCHS, CHCHONO$_2$), 85.6 (CHONO$_2$), 72.8 (CH$_2$—CHS), 70.8 (CH$_2$—CHONO$_2$), 47.8 (CHS), 30.5 (CH$_1$).

Example 6

Synthesis of 5-acetylthio-isosorbide 2-mononitrate (23)

Step 1: Preparation of isoidide-5-monotosylate (20)

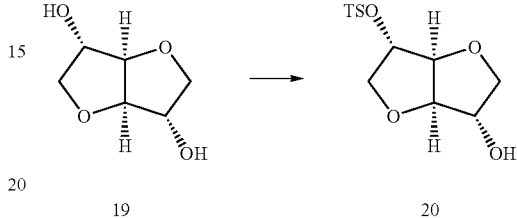

In a 250 mL flask equipped with reflux condenser, compensated pressure addition funnel and magnetic stirring, 10.00 g (68.43 mmol) of isoidide (19) are mixed in 40.0 mL of water and a solution of 13.00 g (68.19 mmol) of p-toluene-sulfonyl chloride in 50.0 mL of toluene is added. An argon atmosphere is formed and the two phases are stirred vigorously, keeping the temperature under 5° C. Under these conditions, a solution of 5.00 g of 85% potassium hydroxide (pellets) in 20.0 mL of water is then dropwise added (while maintaining the internal temperature) for approximately 1 hour and 30 min. The resulting mixture is vigorous stirred at 5° C. for 7 h and protected from light. A white solid precipitates, which is filtered and washed with 4×50.0 mL of water. After drying under reduced pressure, 9.45 g of a white solid are obtained corresponding to the title compound. The liquid resulting from the first filtration is diluted with 250.0 mL of toluene, washed with 4×50.0 mL of water and concentrated to dryness under reduced pressure to yield 7.90 g of a colourless oil corresponding to a mixture of 50% (by $^1$H-NMR) of 5-mono and 2,5-ditosylate isoidide. This crude reaction product is then separated by flash chromatography (CHCl$_3$/AcOEt 4:1→AcOEt 100%), giving rise to the isoidide ditosylate (4.25 g, yield: 31%) followed by 2.50 g of the monotosylate-5-isoidide as a white solid. This process yields 11.95 g of the title compound as a white solid.

$^1$H-NMR (200 MHz, CDCl$_3$): 7.81-7.75 (2H, m, 2CH$_{ar}$), 7.38-7.30 (2H, m, 2CH$_{ar}$), 4.90-4.80 (1H, cs, CHOTs), 4.61 (1H, d, J=3.8 Hz, CH—C—C), 4.52 (1H, d, J=3.6 Hz, CH—O—C), 4.33-4.25 (1H, m, CHOH), 3.98-3.89 (1H, m, H—CHCHOH), 3.86-3.68 (3H, cs, CH$_2$CHOTs, H—CH—CHOH), 2.43 (3H, s, CH$_3$), 1.95 (1H, d, J=4.4 Hz, OH).

$^{13}$C-NMR (50 MHz, CDCl$_3$): 145.36 (C$_{ar}$), 133.13 (C$_{ar}$), 130.09 (2CH$_{ar}$), 127.83 (2CH$_{ar}$), 87.58 (CHCHOH), 84.82 (CHCHOTs), 83.08 (CHOTs), 75.71 (CHOH), 74.72 (CH$_2$ CH$_2$—CHOH), 72.02 (CH$_2$—CHOTs), 21.67 (CH$_3$).

Step 2: Preparation of monotosylate-5-isoidide 2-(tetrahydropyran-2-yl) (21)

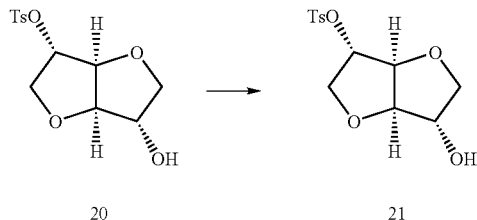

In a 500 mL flask equipped with reflux condenser, a compensated pressure addition funnel and magnetic stirring and a solution of 11.50 g (38.29 mmol) of monotosylate-5-isoidide (20) in 350.0 mL of toluene, are added 6.0 mL of 3,4-dihydro-2H-pyran and 250 mg (0.995 mmol) of pyridinium toluene-4-sulfonate. An argon atmosphere is formed and the mixture is stirred, keeping the internal temperature at 5-10° C. and protected from light, for 7 h. The reaction mixture is washed with 2×100.0 mL of saturated sodium bicarbonate solution. The organic phase is dried over anhydrous MgSO$_4$, filtered and concentrated under reduced pressure, yielding 14.85 g of a colourless oil corresponding to the title compound.

$^1$H-NMR (200 MHz, CDCl$_3$): 7.81-7.75 (2H, m, 2CH$_{ar}$), 7.38-7.30 (2H, m, 2CH$_{ar}$), 4.89-4.81 (1H, m, CHOTs), 4.76-4.52 (3H, cs, CH$_{THP}$, 2CH—O), 4.30-4.22 (1H, m, CH—O—THP), 4.00-3.38 (6H, sc, 2CH$_2$, CH$_2$—O THP), 2.43 (3H, s, CH$_3$), 1.90-1.40 (6H, cs, 3CH$_2$ THP).

$^{13}$C-NMR (50 MHz, CDCl$_3$): 145.25 and 145.20 (C$_{ar}$), 133.29 and 133.22 (C$_{ar}$), 130.03 (2CH$_{ar}$), 127.82 (2CH$_{ar}$), 98.36 and 97.92 (CH$_{THP}$), 86.41 and 85.73 (CHCHOTHP), 85.00 and 84.92 (CHCHOTs), 83.20 and 83.15 (CHOTs), 80.02 and 79.87 (CHOTHP)), 73.54 and 72.31 (CH$_2$CHOTHP), 71.89 (CH$_2$CHOTs), 62.77 and 62.68 (CH$_2$O$_{THP}$), 30.65 and 30.58 (CH$_2$ $_{THP}$), 25.18 (CH$_2$ $_{THP}$), 21.63 (CH$_3$), 19.43 and 19.33 (CH$_2$ $_{THP}$).

Step 3: Synthesis of 5-acetylthio-isosorbide 2-(tetrahydropyran-2-yl) (22)

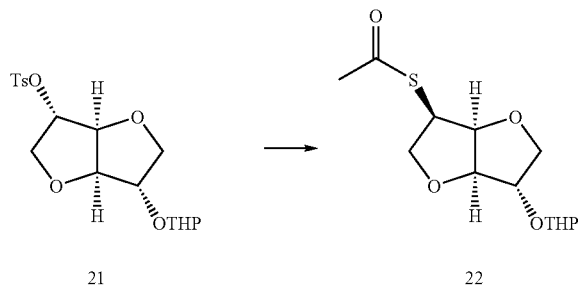

In a 250 mL flask with reflux condenser and mechanical stirring, 8.00 g (20.81 mmol) of monotosylate-5-isoidide 2-(tetrahydropyran-2-yl) (21) are dissolved in 200.0 mL of dimethylformamide, 9.60 g (84.06 mmol) of potassium thioacetate are added, and the mixture is heated under argon atmosphere at 100° C. (bath temperature) for 25 h. The mixture is cooled down to room temperature, diluted with 600.0 mL of toluene and washed with 4×100.0 mL of saturated sodium bicarbonate solution and with 2×100.0 mL of water. The organic phase is dried over anhydrous MgSO$_4$, filtered and concentrated under reduced pressure. After subjecting the crude reaction product to silica gel column chromatography (Hx/AcOEt 4:1), 2.00 g of the title compound are obtained as a yellow oil.

$^1$H-NMR (200 MHz, CDCl$_3$): 4.66-4.38 (3H, cs, CH$_{THP}$, 2CH—O), 4.22-4.14 (1H, m, CHOTHP), 4.05 (1H, ddd, J=8.0 Hz, J=8.0 Hz, J=2.6 Hz, CHS), 3.96-3.28 (6H, cs, 2CH$_2$—O, CH$_2$O$_{THP}$), 2.23 (3H, s, CH$_3$), 1.80-1.28 (6H, cs, 3CH$_2$ $_{THP}$).

$^{13}$C-NMR (50 MHz, CDCl$_3$): 194.73 (C=O), 98.04 and 97.63 (CH$_{THP}$), 87.24 and 86.82 (CHCHOTHP (3) ), 82.42 and 82.15 (CH—CHS), 80.94 and 80.91 (CHOTHP), 73.87 and 72.83 (CH$_2$—CHOTHP), 71.02 and 70.88 (CH$_2$—CHS (6) ), 62.37 and 62.29 (CH$_2$O$_{THP}$), 46.00 and 45.73 (CHS), 30.38 (CH$_2$ $_{THP}$), 30.11 (CH$_3$), 24.97 (CH$_2$ $_{THP}$), 19.14 (CH$_2$ $_{THP}$).

Step 4: Preparation of 5-acetylthio-isosorbide 2-mononitrate (23)

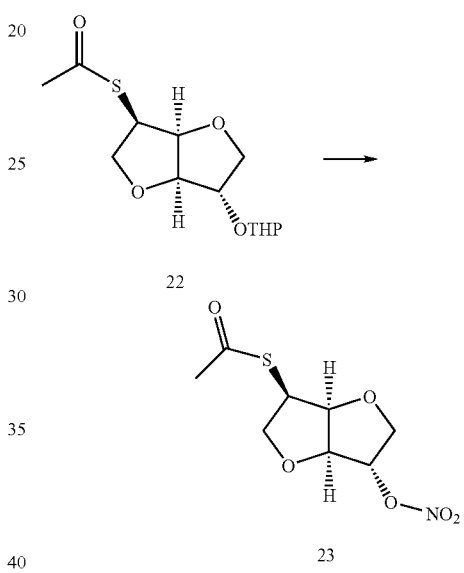

A nitrating mixture is prepared, carefully adding 0.9 mL of 60% nitric acid over a mixture of 3.6 mL of acetic anhydride and 0.9 mL of acetic acid. Preparation is carried out maintaining an internal temperature of 0-5° C. In a 25.0 mL flask with reflux condenser, a compensated pressure addition funnel and magnetic stirring, 1.80 g (6.24 mmol) of (22) in 4.5 mL of toluene and 0.9 mL of acetic acid are dissolved at a temperature of 20° C. Then, the previously prepared nitrating mixture is dropwise added maintaining an internal temperature of 30-35° C. The resulting mixture is stirred for 3 h, cooled, diluted with 100.0 mL of toluene and washed with 25.0 mL of saturated sodium chloride solution. Then, 15.0 mL of methanol are added and the organic phase is washed with 3×25.0 mL of saturated sodium bicarbonate solution. The organic phase is dried over anhydrous MgSO$_4$, filtered and concentrated under reduced pressure. After subjecting the crude reaction product to silica gel column chromatography (Hx/AcOEt 5:1), 1.19 g of the title compound are obtained as a yellow-transparent oil.

$^1$H-NMR (200 MHz, CDCl$_3$): 5.37-5.30 (1H, cs, CHONO$_2$), 4.74-4.63 (m, 2H, CHCHONO$_2$, CHCHS), 4.27-4.92 (4H, cs, CHS, H—CHCHS, CH$_2$—CHONO$_2$), 3.58-3.46 (m, 1H, H—CHCHS), 2.33 (s, 3H, CH$_3$).

$^{13}$C-NMR (50 MHz, CDCl$_3$): 194.60 (C=O), 86.31 (CHONO$_2$), 84.75 (CHCHONO$_2$), 82.89 (CHCHS), 71.61 (CH$_2$—CHS), 71.53 (CH$_2$—CHONO$_2$), 45.82 (CHS), 30.37 (CH$_3$).

The invention claimed is:

1. A method for the preparation of a compound of formula (I):

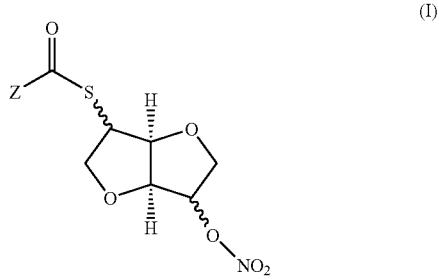

(I)

wherein Z represents a $C_{1-6}$-alkyl, $C_{2-6}$-alkenyl, $C_{3-8}$-cycloalkyl, aryl, heteroaryl, aryl $C_{1-6}$-alkyl, or heteroaryl-$C_{1-6}$-alkyl group, optionally substituted by one to three groups independently selected from the group consisting of halogen, $C_{1-6}$-alkyl and $C_{1-6}$-alkylthio,
said method comprising:
reacting a compound of formula (II):

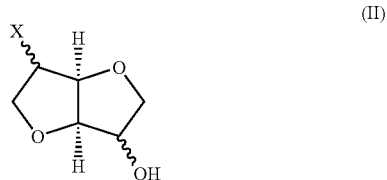

(II)

wherein X represents halogen, cyano, methanesulfonyloxy, p-toluenesulfonyloxy or trifluoromethanesulfonyloxy,
with a compound of formula (IIIa) or (IIIb):

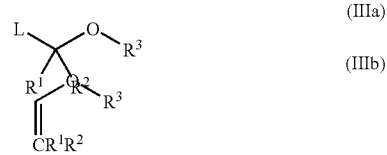

(IIIa)
(IIIb)

wherein:
L represents halogen, cyano, methanesulfonyloxy, p-toluenesulfonyloxy or trifluoromethanesulfonyloxy; and
$R^1$, $R^2$ and $R^3$ independently from each other represent hydrogen, $C_{1-6}$-alkyl, $C_{2-6}$-alkenyl, $C_{3-8}$-cycloalkyl, $C_{4-8}$-cycloalkenyl, $(C_{1-6}$-alkyl)-$C_{3-8}$-cycloalkyl, $(C_{1-6}$-alkyl)-$C_{4-8}$-cycloalkenyl, phenyl or $(C_{1-6}$-alkyl)-phenyl, or $R^2$ and $R^3$ together form a 5-, 6- or 7-membered ring, then treating the obtained product with a thiocarboxylic acid of formula (IV) or a salt thereof:

(IV)

wherein Z is as defined above, and
subsequently carrying out a nitration reaction.

2. The method according to claim 1, wherein in the compound of formula (I) the thiocarboxylate Z—C(=O)—S— group is cis to the nitrate group.

3. The method according to claims 1 or 2, wherein Z represents a $C_{1-6}$-alkyl, $C_{2-6}$-alkenyl, aryl, or heteroaryl group.

4. The method according to claim 3, wherein Z is selected from the group consisting of methyl, ethyl, n-propyl, and n-butyl.

5. The method according to claim 4, wherein Z represents a methyl group.

6. The method according to claims 1 or 2, wherein in formula (IIIa) L represents halogen, and $R^1$, $R^2$ and $R^3$ independently represent hydrogen or $C_{1-6}$ alkyl.

7. The method according to claims 1 or 2, wherein in formula (IIIb) $R^1$ represents hydrogen or $C_{1-6}$ alkyl and $R^2$ and $R^3$ together with the carbon atoms to which they are attached and with the oxygen atom attached to the oxygen form a 5-, 6- or 7-membered ring.

8. The method according to claim 6, wherein formula (IIIa) represents bromomethyl-methylether.

9. The method according to claim 7, wherein formula (IIIb) represents 3,4-dihydro-2H-pyran or ethyl-vinyl-ether.

10. The method according to claims 1 or 2, wherein the treatment with the thiocarboxylic acid of formula (IV) or a salt thereof is carried out without isolation of the product obtained by reaction of compound (II) with compound (IIIa) or (IIIb).

11. The method according to claims 1 or 2, wherein the thiocarboxylic acid of formula (IV) is used as its salt with an alkali metal or an earth alkali metal, selected from the group consisting of sodium, potassium, cesium, magnesium and calcium.

12. The method according to claim 11 wherein the thiocarboxylic acid of formula (IV) is used in the form of its potassium salt.

13. A compound according to formula (3') or (4'):

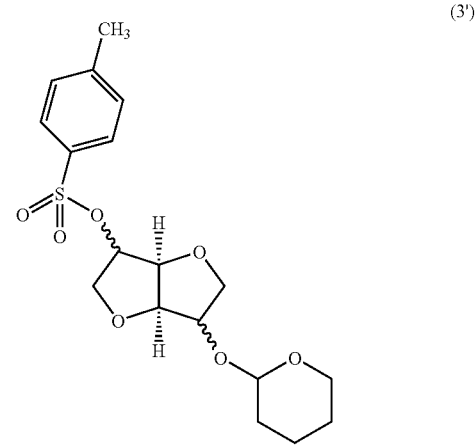

(3')

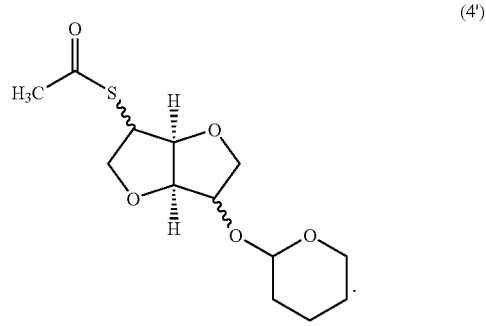

(4')

* * * * *